United States Patent [19]
Ross et al.

[11] Patent Number: 5,833,643
[45] Date of Patent: *Nov. 10, 1998

[54] APPARATUS FOR PERFORMING OPHTHALMIC PROCEDURES

[75] Inventors: Rod Ross, Laguna Niguel; Greggory Hughes, Fountain Valley; James C. Boore, Poway, all of Calif.

[73] Assignee: Scieran Technologies, Inc., Laguna Niguel, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 972,828

[22] Filed: Nov. 18, 1997

Related U.S. Application Data

[63] Continuation of Ser. No. 660,520, Jun. 7, 1996, abandoned.
[51] Int. Cl.⁶ ................................................. A61B 17/32
[52] U.S. Cl. ............................................. 604/22; 606/171
[58] Field of Search .............................. 604/22; 606/170, 606/171; 600/568; 30/43.92, 215, 216

[56] References Cited

U.S. PATENT DOCUMENTS

| Re. 23,496 | 5/1952 | Seeler . |
| 1,841,968 | 1/1932 | Lowry . |
| 1,847,658 | 3/1932 | Lasker . |

(List continued on next page.)

FOREIGN PATENT DOCUMENTS

| 2 549 727 | of 0000 | European Pat. Off. . |
| 2547185 | 4/1977 | Germany . |

OTHER PUBLICATIONS

Brochure, Site TXR Systems, Site Mycrosurgical Systems, Inc., Horsham, Pennsylvania.

Parks, "Intracapsular Asoiration" article, pp. 59–74.

Van Oldenborgh, "Correction of Late Operative Complicatings by Means of a Suction Cutter," Ophthal. Soc. U.K. (1980), 100, 219, pp. 219–221.

Helfgott, "A System for Variable Aspiration of Material Dissected from the Posterior Chamber", Ophthalmic Surgery, vol. 15, Jun. 1984, pp. 529–530.

Murayama et al. "A Portable Air Driving Unit for Blood Pumps", Japanese Journal of Artificial Organs, vol. 14, No. 3, pp. 1206–1209 (English translation).

(List continued on next page.)

*Primary Examiner*—Michael H. Thaler
*Attorney, Agent, or Firm*—Blakely Sokoloff Taylor & Zafman

[57] ABSTRACT

A surgical tissue cutter. The cutter includes an inner sleeve that moves adjacent to an outer port of an outer sleeve. The outer port is coupled to a source of vacuum that pulls tissue into the outer port when the inner sleeve is moved away from the port. The inner sleeve then moves across the outer port and severs the tissue in a guillotine fashion. The inner sleeve is coupled to a rotating output shaft of a motor by a wobble plate which induces an oscillating translational movement of the sleeve in response to a rotation of the output shaft. The motor speed is controlled by a foot pedal which allows the surgeon to directly control the cutting speed of the device. The wobble plate can be replaced to vary the stroke and duty cycle of the inner sleeve. The inner sleeve is coupled to an aspiration line that pulls the severed tissue out of the cutter. The level of the aspiration vacuum pressure can be controlled by varying the speed of the motor and the movement of the inner sleeve. The inner sleeve functions as both a cutter and a control valve that controls the flow of fluid through the outer port. Controlling the fluid flow at the outer port provides a vacuum control system that has an almost instantaneous response time.

4 Claims, 2 Drawing Sheets

U.S. PATENT DOCUMENTS

| | | |
|---|---|---|
| 2,070,281 | 2/1937 | Leggiadro . |
| 2,708,437 | 5/1955 | Hutchins . |
| 2,824,455 | 2/1958 | Ristow et al. . |
| 3,033,196 | 5/1962 | Hay . |
| 3,252,623 | 5/1966 | Corbin et al. . |
| 3,266,494 | 8/1966 | Brownrigs et al. . |
| 3,308,828 | 3/1967 | Pippin . |
| 3,399,677 | 9/1968 | Gould et al. . |
| 3,561,429 | 2/1971 | Jewett . |
| 3,624,821 | 11/1971 | Henderson . |
| 3,693,613 | 9/1972 | Kelman . |
| 3,752,161 | 8/1973 | Bent . |
| 3,763,862 | 10/1973 | Spieth . |
| 3,815,604 | 6/1974 | O'Malley et al. . |
| 3,842,839 | 10/1974 | Malis et al. . |
| 3,884,238 | 5/1975 | O'Malley et al. . |
| 3,899,829 | 8/1975 | Storm et al. . |
| 3,903,881 | 9/1975 | Weigl . |
| 3,913,584 | 10/1975 | Walchle et al. . |
| 3,920,014 | 11/1975 | Banko . |
| 3,930,505 | 1/1976 | Wallach . |
| 3,977,425 | 8/1976 | Hayashida . |
| 3,982,539 | 9/1976 | Muriot . |
| 3,986,512 | 10/1976 | Walliser . |
| 4,004,590 | 1/1977 | Muriot . |
| 4,108,182 | 8/1978 | Hartman et al. ............... 606/171 |
| 4,135,515 | 1/1979 | Muriot . |
| 4,137,920 | 2/1979 | Bonnet . |
| 4,168,707 | 9/1979 | Douvas et al. . |
| 4,178,707 | 12/1979 | Littlefield . |
| 4,204,328 | 5/1980 | Kutner . |
| 4,210,146 | 7/1980 | Banko . |
| 4,217,993 | 8/1980 | Jess et al. . |
| 4,223,676 | 9/1980 | Wuchinich et al. . |
| 4,245,815 | 1/1981 | Willis . |
| 4,246,902 | 1/1981 | Martinez ..................... 606/171 X |
| 4,274,411 | 6/1981 | Dotson, Jr. . |
| 4,308,835 | 1/1982 | Abbey . |
| 4,314,560 | 2/1982 | Helfgott et al. . |
| 4,320,761 | 3/1982 | Haddad . |
| 4,354,838 | 10/1982 | Hoyer et al. . |
| 4,395,258 | 7/1983 | Wang et al. . |
| 4,396,386 | 8/1983 | Kurtz et al. . |
| 4,428,748 | 1/1984 | Peyman et al. ............ 606/171 X |
| 4,445,517 | 5/1984 | Field . |
| 4,474,411 | 10/1984 | Peters et al. . |
| 4,475,904 | 10/1984 | Wang . |
| 4,493,695 | 1/1985 | Cook . |
| 4,493,698 | 1/1985 | Wang et al. . |
| 4,522,371 | 6/1985 | Fox et al. . |
| 4,524,948 | 6/1985 | Hall . |
| 4,530,357 | 7/1985 | Pawloski et al. . |
| 4,540,406 | 9/1985 | Miles . |
| 4,589,414 | 5/1986 | Yoshida et al. ................ 606/171 |
| 4,598,729 | 7/1986 | Naito et al. . |
| 4,706,687 | 11/1987 | Rogers . |
| 4,723,545 | 2/1988 | Nixon et al. . |
| 4,757,814 | 7/1988 | Wang et al. . |
| 4,768,506 | 9/1988 | Parker et al. . |
| 4,770,654 | 9/1988 | Rogers et al. . |
| 4,838,281 | 6/1989 | Rogers et al. . |
| 4,943,289 | 7/1990 | Goode et al. . |
| 4,988,347 | 1/1991 | Goode et al. . |
| 5,011,482 | 4/1991 | Goode et al. . |
| 5,013,310 | 5/1991 | Goode et al. . |
| 5,059,204 | 10/1991 | Lawson et al. . |
| 5,201,749 | 4/1993 | Sachse et al. . |
| 5,207,683 | 5/1993 | Goode et al. . |
| 5,273,524 | 12/1993 | Fox et al. . |
| 5,354,268 | 10/1994 | Peterson et al. . |
| 5,364,395 | 11/1994 | West, Jr. . |
| 5,380,280 | 1/1995 | Peterson . |
| 5,403,276 | 4/1995 | Schechter et al. . |
| 5,476,473 | 12/1995 | Heckele . |
| 5,507,751 | 4/1996 | Goode et al. . |
| 5,520,684 | 5/1996 | Imran . |
| 5,527,332 | 6/1996 | Clement . |
| 5,531,744 | 7/1996 | Nardella et al. . |

OTHER PUBLICATIONS

Scuderi, et al., French article entitled La Chirurgie de la Cartaracte Congenitale, pp. 174–185. (English translation).

Hayashi et al., Japanese Experience with Ventricular Assist Devices IBEE Engineering in Medicine and Biology Magazine Mar. 1986, pp. 30–36.

Grieshaber and Co. of Switzerland, Sutherland Rotatable Intraocular Microscissors, 2 pages.

Micro–Vit Vitrectomy System Product Brochure and Instruction Manual.

Storz Irrigation Aspiration System Product Brochure and Instruction Manual.

United Surgical Corporation Brochure on "Phacotron Plus", one page.

Surgical Design Company Brochure on Keates Ultrasonic I/E Mini Probe by A. Banko, 2 pages.

Surgical Design Corporation Brochure on U.S., Phaco System, 1 page.

Coopervision Brochure on System V1, 1 page.

Coopervision Brochure on Cavitron/Kelman Model 6500 EIS and Model 7500, 6 pages.

Surgical Design Brochure on "The Ocusystem", 1 page.

Coopervision Brochure on Cavitron/Kelman Phaco–Emulsifier Aspirator Model 8001, 2 pages.

Coopervision Brochure on Cavitron/Kelman Phaco–Emulsifier Aspirator Model 9001, 6 pages.

Greishaber of Switzerland Brochure on "MPC, The Membrane Peeler Cutter", 5 pages.

Charles and Wang, "A Linear Suction Control for the Vitreous Cutter (Ocutome)", Arch. Ophthalmol. vol. 99, Sep. 1981, p. 1631.

Crosby, "On Control of Artificial Hearts", pp. 89–114.

Mrava, Cardiac Engineering, vol. 3, pp. 31–68.

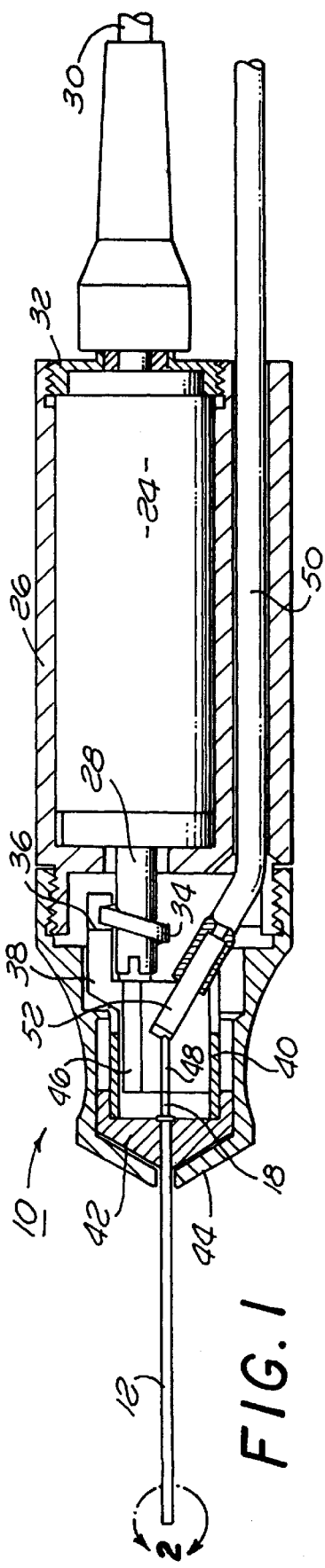
FIG. 1
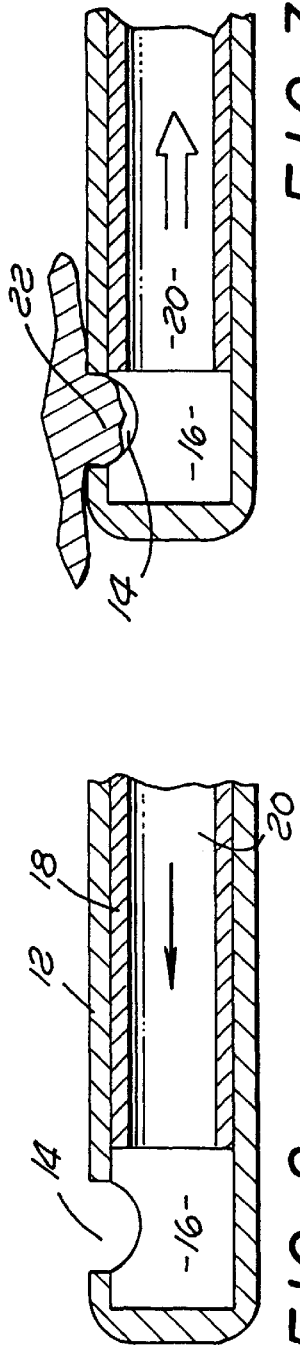
FIG. 2
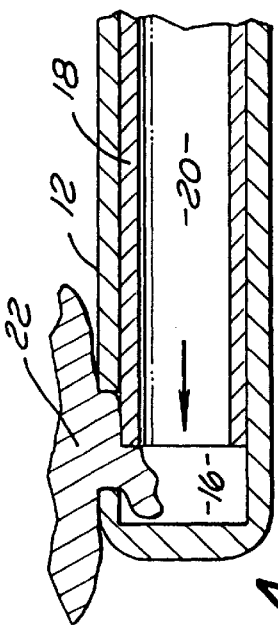
FIG. 3
FIG. 4

APPARATUS FOR PERFORMING OPHTHALMIC PROCEDURES

This is a Continuation Application of application Ser. No. 08/660,520, filed Jun. 7, 1996 now abandoned.

BACKGROUND OF THE INVENTION

1. Field of the Invention

The present invention relates to a surgical system for cutting tissue.

2. Description of Related Art

There are many surgical procedures that require the cutting and aspiration of tissue. For example, in a retina re-attachment procedure the surrounding vitreo tissue must be removed before the retina is repaired. The cutting device must be delicate enough to remove the tissue without further damaging the retina. Prior art ophthalmic cutting devices include an inner sleeve that moves relative to an outer port of an outer sleeve. The sleeves are coupled to a vacuum system which pulls tissue into the outer port when the inner sleeve moves away from the port. The inner sleeve then moves in a reverse direction past the outer port to sever the tissue in a guillotine fashion. The vacuum system draws the severed tissue away from the outer port so that the process can be repeated.

The inner sleeve is driven by a motor located within a hand piece that is held by the surgeon. The inner sleeve is typically coupled to the motor by a rotating lever mechanism. Rotating lever mechanisms of the prior art are relatively large and complex. Additionally, the stroke and duty cycle of the inner sleeve is fixed for each device. It would be desirable to provide a surgical guillotine cutter that is inexpensive to produce, small in size and would allow a surgeon to vary the stroke and duty cycle of the inner cutter.

Guillotine cutters are typically provided with a control system that allows the surgeon to vary the vacuum pressure of the aspiration line. U.S. Pat. Nos. 4,395,258; 4,493,698; 4,706,687 and 4,838,281 issued to Wang et al. and Rogers et al., respectively, disclose systems for controlling the vacuum pressure of a guillotine cutter. The Wang/Rogers systems include a solenoid actuated valve that is coupled to the hand piece and controls the flow of fluid in the aspiration system. The position of the valve and the corresponding vacuum of the system is controlled by an input signal provided to the solenoid by a control circuit. The input signal is typically the summation of a feedback signal and a control signal that is generated by a potentiometer. The feedback signal corresponds to the actual vacuum pressure measured in the system. The potentiometer is typically a foot pedal that is manipulated by the surgeon.

The surgeon controls the vacuum pressure by depressing the foot pedal and varying the amount of air flow through the solenoid control valve. Because of the inertia within the system, there is typically a lag between the input command of the surgeon and the actual variation of vacuum pressure at the tip of the cutter. It would be desirable to provide a vacuum control system that has a more rapid response time than systems of the prior art.

SUMMARY OF THE INVENTION

The present invention is a surgical tissue cutter. The cutter includes an inner sleeve that moves adjacent to an outer port of an outer sleeve. The inner sleeve is coupled to a source of vacuum that pulls tissue into the outer port when the inner sleeve is moved away from the port. The inner sleeve then moves across the outer port and severs the tissue in a guillotine fashion. The inner sleeve is coupled to a rotating output shaft of a motor by a wobble plate which induces an oscillating translational movement of the sleeve in response to a rotation of the output shaft. The motor speed is controlled by a foot pedal which allows the surgeon to directly control the cutting speed of the device. The wobble plate can be replaced to vary the stroke and duty cycle of the inner sleeve.

The inner sleeve is coupled to an aspiration line that pulls the severed tissue out of the cutter. The level of the aspiration vacuum pressure can be controlled by varying the speed of the motor and the movement of the inner sleeve. The inner sleeve functions as both a cutter and a control valve that controls the flow of fluid through the outer port. Controlling the fluid flow at the outer port provides a vacuum control system that has an almost instantaneous response time.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 1 is a cross-sectional view of surgical guillotine cutter of the present invention;

FIG. 2 is an enlarged cross-sectional view of the tip of the cutter;

FIG. 3 is an enlarged view similar to FIG. 2 showing tissue being drawn into an outer port of the cutter;

FIG. 4 is a an enlarged view similar to FIG. 2 showing an inner sleeve severing the tissue drawn into the outer port;

DETAILED DESCRIPTION OF THE INVENTION

Figure 5:
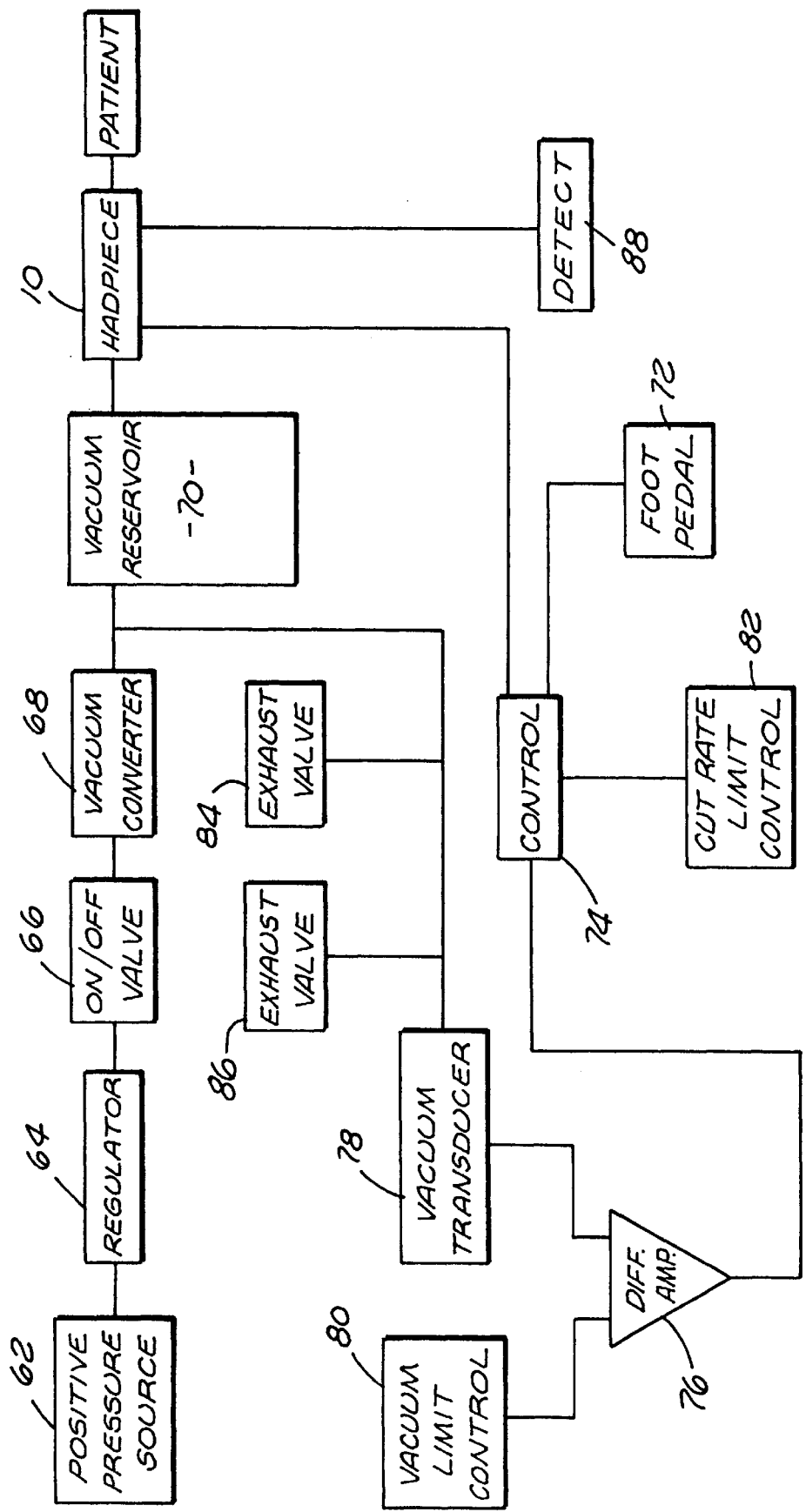
FIG. 5 is a schematic of a vacuum control system for the cutter.

Referring to the drawings more particularly by reference numbers, FIGS. 1 and 2 show a surgical guillotine cutter 10 of the present invention. The cutter 10 is used to remove and aspirate tissue. For example, the cutter 10 can be used to remove intraocular tissue during an ophthalmic procedure to re-attach a retina of an eye. Although use in an ophthalmic procedure is described, it is to be understood that the cutter 10 can be used to cut and aspirate other tissue.

Referring to FIG. 2, the cutter 10 includes an outer sleeve 12 that has an outer port 14. The outer port 14 is in fluid communication with an inner channel 16 of the sleeve 12. Located within the inner channel 16 of the outer sleeve 12 is an inner sleeve 18. The inner sleeve 18 has an inner channel 20 that is in fluid communication with an aspiration system. The aspiration system creates a vacuum pressure that pulls tissue into the outer port 14 when the inner sleeve 18 is located away from the port 14. The inner sleeve 18 moves within the inner channel 16 of the outer sleeve 12 to cut tissue that is pulled into the outer port 14 by the aspiration system.

FIGS. 3 and 4 show tissue 22 that is cut by the cutter 10. The inner sleeve 18 is initially moved away from the outer port 14 and the vacuum pressure pulls tissue 22 into the port 14 and the inner channel 16. The inner sleeve 18 then moves toward the outer port 14 and severs the tissue 22 within the inner channel 16. The severed tissue is pulled through the inner channel 20 of the inner sleeve 18 by an aspiration system. The inner sleeve 18 then moves away from the outer sleeve 14 wherein the cutting process is repeated.

The movement of the inner sleeve 18 also controls the flow of fluid through the outer port 14 and into the aspiration system. Increasing the cutting speed decreases the flow rate and vice versa. The flow of fluid through the opening 14 may vary the vacuum pressure within the aspiration system. In addition to varying the cutting speed the surgeon may also vary the vacuum pressure by changing the speed of the motor and the flow of fluid through the opening 14. The cutting device 10 of the present invention can thus control the vacuum pressure within the aspiration system by controlling the oscillation speed of the inner sleeve 14.

Referring to FIG. 1, the cutter 10 includes a motor 24 that is located within a hand piece 26. Extending from an end of the motor 24 is a rotating output shaft 28. The motor 24 is preferably an electrical device that is coupled to an external power source by wires 30 that are attached to a plug 32 screwed into the hand piece 26. The rotational speed of the output shaft 28 is a function of the amplitude of an input signal that is provided by wires 30. Although an electrical motor is described, it is to be understood that the motor may be a pneumatic device.

The cutter 10 has a wobble plate 34 that attached to the output shaft 28 of the motor 24. The wobble plate 34 is located within a groove 36 of a slider 38. The slider 38 is attached to the inner sleeve 18. Rotation of the output shaft 28 spins the wobble plate 34, which induces an oscillating translational movement of both the slider 38 and the inner sleeve 18. The motor 24 and wobble plate 34 move the inner sleeve 14 in an oscillating manner to cut tissue as shown in FIGS. 3 and 4.

The slider 38 moves within a bearing sleeve 40 that is captured by an inner cap 42 and an outer cap 44 of the cutter 10. The outer cap 44 is screwed onto the hand piece 26. The slider 38 may have an aperture 46 that extends therethrough to allow air to flow out of the area between the slider 38 and the inner cap 42. The aperture 46 prevents the formation of a back pressure that may impede the movement of the slider 38. The slider 38 further has a channel 48 that is coupled to an aspiration line 50 by a tube 52. The channel 48 provides fluid communication between the aspiration line 50 and the inner channel 20 of the inner sleeve 18.

The stroke and the duty cycle of the inner sleeve 18 are related to the cam angle and profile of the wobble plate 34. The stroke and/or duty cycle can be varied by removing the cap 44 and replacing the wobble plate 34 with a new part which has a different cam angle and/or profile. The present invention thus allows a surgeon to readily change the duty cycle and stroke of the device 10.

FIG. 5 shows a system 60 for controlling the vacuum pressure within the cutter 10. The system includes a positive pressure source 62 which creates a positive pressure. The output of the positive pressure source 62 may be regulated by a regulator 64. The regulator 64 may be coupled to a shut-off valve 66 that can de-couple the source 62 from the remaining portion of the system 60.

The positive pressure created by the pump 62 is converted into a negative vacuum pressure by a converter 68. The converter 68 may be a venturi pump that is relatively linear in operation. The system 60 may have a reservoir 70 that is coupled to the converter 68 and the aspiration line 50 of the cutter 10. The converter 68 creates a vacuum pressure within the aspiration line 50 of the cutter 10, to pull the tissue into the outer port 14 of the outer sleeve 12, and to aspirate the severed tissue.

The system 60 includes a potentiometer 72 which provides a variable input signal to the motor 24 of the cutter 10. The potentiometer 72 is typically a foot pedal which can be manipulated by the surgeon to vary the input signal and the speed of the motor 24. Varying the speed of the motor 24 changes the oscillation frequency of the inner sleeve 18, the flow of fluid through the outer port 14 and the vacuum pressure within the system. The surgeon can therefore control the flow of fluid through the aspiration system by manipulating the foot pedal 72 and varying the motor speed of the cutter 10.

The potentiometer 72 may be coupled to the motor by a control circuit 74. The control circuit 74 is coupled to the output of a differential amplifier 76. One input of the differential amplifier 76 is coupled to a transducer 78 that senses the vacuum pressure within the system. The transducer 78 provides an output signal that corresponds to the magnitude of the vacuum pressure. The other input of the differential amplifier 76 may be connected to a vacuum limit control 80 which limits the level of the vacuum pressure. The differential amplifier 76 and transducer 78 provide a closed loop feedback signal for the aspiration system.

The control circuit 74 compares the feedback signal provided by the differential amplifier 76 with the control signal provided by the potentiometer 72 and generates the input signal for the aspiration system. The control circuit 74 typically adds, the difference between the feedback signal and the control signal from the foot pedal, to the control signal. The control circuit 74 may include a differential amplifier and adder connected as shown in U. S. Pat. No. 4,838,281, which is hereby incorporated by reference. The system 60 may include a variable cut rate limit control circuit 82 that limits the amplitude of the motor input signal and allows the surgeon to control the minimum and maximum cutting speed of the cutter 10.

The system 60 may have a first solenoid exhaust valve 84 that bleeds off the vacuum line to decrease the magnitude of the vacuum pressure. The valve 84 may be coupled to the control circuit 74 to lower the magnitude of the vacuum pressure when the actual pressure level exceeds a desired pressure level. The system 60 may also have a second solenoid exhaust valve 86 that quickly returns the system to atmospheric pressure. The shut-off valve 66 and second exhaust valve 86 can be coupled to the potentiometer 72 so that the shut-off valve 66 is closed and the exhaust valve 86 is opened when the surgeon releases the foot pedal 72 and moves the potentiometer to an off position. Returning the system to atmospheric pressure prevents a sudden vacuum surge when the surgeon again utilizes the cutter 10 at a surgical site.

The system 10 may also have an off detect circuit 88 which drives the motor 24 and moves the inner sleeve 18 to close the outer port 14 when the surgeon releases the foot pedal 72. Closing the outer port 14 prevents the residual vacuum of the system from pulling in tissue when the cutter 10 has been inactivated. The detect circuit 88 may drive one of the motor coils when the foot pedal is released to move the inner sleeve 18 to an extended position that closes the outer port 14.

In operation, a surgeon may insert the outer sleeve 12 into an eye to perform an ophthalmic procedure. The surgeon may remove intraocular tissue by depressing the foot pedal 72 and initiating the cutting action of the cutter 10. The cutting speed and fluid flow can be varied by manipulating the foot pedal 72 and varying the motor speed of the cutter. Valving the vacuum pressure at the outer port 14 of the cutter provides an almost instantaneous response time for varying the fluid flow at the surgical site. Releasing the foot pedal 72 closes the shut-off valve 66 and opens the exhaust valve 88 to return the system 60 to atmospheric pressure.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

By way of example, the aspiration line 50 and/or reservoir 70 may be directly coupled to the intake port of a linear pump. The potentiometer 72 and/or control circuit 74 may provide an input signal to control the output of the linear pump and the vacuum pressure within system. The linear pump may be a device sold by Medo of Woodale, Ill. under the part designation VP0660. In this embodiment, the vacuum pressure may also be further regulated by controlling the motor speed of the cutter 10.

Although a control circuit 74 is shown and described, it is to be understood that the foot pedal 72 can be connected directly to the motor 24 without a feedback input. Additionally, although a foot pedal 72 is shown and described, it is to be understood that the motor 24 could be controlled by a handpiece.

What is claimed is:

1. A surgical device, comprising:

a hand piece;

an outer sleeve mounted to said hand piece, said outer sleeve having an outer port;

a motor located within said hand piece, said motor having a rotating output shaft;

an inner sleeve that moves within said outer sleeve;

a slider that is attached to said inner sleeve, said slider having a groove;

a wobble plate that is attached to said rotating output shaft of said motor and located within said groove of said slider to induce an oscillating translational movement of said inner sleeve in response to a rotational movement of said output shaft; and, a cap that is attached to said hand piece to enclose said slider and said wobble plate, said slider and said wobble plate are exposed when said cap is removed from said hand piece so that said slider and said inner sleeve can be detached from said wobble plate.

2. The device as recited in claim 1, further comprising a bearing sleeve that guides said slider.

3. The device as recited in claim 1, further comprising an aspiration line that is connected to said slider and is in fluid communication with said outer port.

4. The device as recited in claim 1, wherein said slider has an aperture that extends through said slider.

* * * * *